(12) United States Patent
Lambert et al.

(10) Patent No.: US 12,239,801 B2
(45) Date of Patent: Mar. 4, 2025

(54) PROTECTIVE DRESSING

(71) Applicant: EMED Technologies Corporation, El Dorado Hills, CA (US)

(72) Inventors: Paul Lambert, El Dorado Hills, CA (US); Carlos Gutierrez, El Dorado Hills, CA (US)

(73) Assignee: Bio Health Frontiers, Inc., El Dorado Hills, CA (US)

( * ) Notice: Subject to any disclaimer, the term of this patent is extended or adjusted under 35 U.S.C. 154(b) by 373 days.

(21) Appl. No.: 17/285,879

(22) PCT Filed: Oct. 16, 2019

(86) PCT No.: PCT/US2019/056574
§ 371 (c)(1),
(2) Date: Apr. 15, 2021

(87) PCT Pub. No.: WO2020/081712
PCT Pub. Date: Apr. 23, 2020

(65) Prior Publication Data
US 2021/0346650 A1    Nov. 11, 2021

Related U.S. Application Data

(60) Provisional application No. 62/746,372, filed on Oct. 16, 2018.

(51) Int. Cl.
*A61M 25/02* (2006.01)
*A61F 13/00* (2024.01)
*A61F 13/02* (2024.01)

(52) U.S. Cl.
CPC ......... *A61M 25/02* (2013.01); *A61F 13/0266* (2013.01); *A61F 2013/00412* (2013.01);
(Continued)

(58) Field of Classification Search
CPC .......... A61M 25/02; A61M 2025/0273; A61M 2025/0246; A61M 2025/0253;
(Continued)

(56) References Cited

U.S. PATENT DOCUMENTS

| | | |
|---|---|---|
| 4,753,232 A | 6/1988 | Ward |
| 4,926,850 A | 5/1990 | Lott et al. |

(Continued)

FOREIGN PATENT DOCUMENTS

EP          0630629          12/1994

OTHER PUBLICATIONS

International Search Report issued on International Patent Application No. PCT/US2019/056574, dated Feb. 6, 2020.
(Continued)

*Primary Examiner* — Caitlin A Carreiro
(74) *Attorney, Agent, or Firm* — Jones Day

(57) ABSTRACT

A transparent dressing includes a portion without adhesive to allow placement over a catheter to reduce any effect of placing and positioning of a catheter at the time of removal of the dressing. The transparent dressing may include at least one tab for handling and removing the dressing, the at least one tab being positioned on at least one outer edge of the dressing.

19 Claims, 2 Drawing Sheets

(52) U.S. Cl.
CPC ............... *A61F 2013/00663* (2013.01); *A61F 2013/00846* (2013.01); *A61M 2025/0273* (2013.01)

(58) Field of Classification Search
CPC ........ A61M 2025/0266; A61F 13/0259; A61F 13/0266; A61F 13/025; A61F 13/024; A61F 13/0236; A61F 13/02; A61F 13/00; A61F 13/00021; A61F 13/0246; A61F 13/0253; A61F 13/0269; A61F 13/0276; A61F 13/0283; A61F 13/0289; A61F 13/60; A61F 2013/00412; A61F 2013/00663; A61F 2013/00846; A61F 2013/00655; A61F 2013/008; A61F 2013/00817; A61F 2013/00089; A61F 2013/00582; A61F 15/00; A61F 15/008; B32B 38/10
USPC .... 602/41–42, 52, 54, 57, 58, 900; 128/877, 128/878, 879, 888–894
See application file for complete search history.

(56) References Cited

U.S. PATENT DOCUMENTS

| | | | | |
|---|---|---|---|---|
| 5,160,315 | A | * 11/1992 | Heinecke | A61F 13/023 602/57 |
| 6,169,224 | B1 | 1/2001 | Heinecke et al. | |
| 6,224,571 | B1 | * 5/2001 | Bierman | A61M 25/02 604/174 |
| 2004/0220505 | A1 | * 11/2004 | Worthley | A61M 25/02 602/57 |
| 2012/0238932 | A1 | * 9/2012 | Atteia | A61F 13/0276 156/247 |
| 2013/0310754 | A1 | * 11/2013 | Kutsch | A61M 25/02 604/180 |

OTHER PUBLICATIONS

Supplementary European Search Report issued on EP Application No. 19874372 dated Jun. 18, 2022 (5 pages).

\* cited by examiner

PROTECTIVE DRESSING

CROSS-REFERENCE TO RELATED APPLICATIONS

The present application claims the benefit of and priority to U.S. Provisional Patent Application No. 62/746,372 entitled "Protective Dressing" filed on Oct. 16, 2018, the foregoing application being incorporated herein, by reference, in its entirety.

FIELD

The disclosure relates generally to protective dressings. The disclosure relates specifically to protective dressings with a transparent window.

BACKGROUND

Dressings are used to cover wounds and catheterization sites. The dressings can have pressure-sensitive adhesives on the portion of the dressing that is in contact with the patient. The dressing can provide protection from infection. The dressing can be used to stabilize the injection site of the catheter to decrease the likelihood of the needle being pulled out of the patient. Transparent dressing allows visual inspection of the wound or catheterization site. This is an improvement over non-transparent dressings, such as a bandage or gauze and tape, that must be lifted or removed to view the wound or catheterization site. The dressing often needs to be changed upon lifting or removal. Not having to lift the dressing can decrease the likelihood of infection. Therefore, transparent dressings provide clinical and economic advantages over non-transparent dressings.

It would be advantageous to have a dressing that possesses a transparent window without adhesive and other areas on the surface of the dressing that is in contact with the patient to allow increased handleability.

SUMMARY

An embodiment of the disclosure is a protective dressing comprising a backing; a transparent film adjacent to the backing wherein a portion of the transparent film does not have an adhesive coating and a portion of the transparent film does have an adhesive coating; at least two protective tabs adjacent to the transparent film wherein the protective tabs are each present at opposite ends of the transparent film and do not have an adhesive coating; and a stabilizing layer adjacent to the transparent film wherein the stabilizing layer extends around upper perimeter of the transparent film and is present across only a portion or a subset of the entire upper surface of the transparent film, wherein the interior border of the stabilizing layer has one side that is dissimilar to the opposite side, wherein the one side has a split in the stabilizing layer.

In an embodiment, the stabilizing layer comprises a split.

Optionally, the transparent film is at least one of a polymeric film, a polyester film, a polyurethane film, and combinations thereof.

Optionally, the transparent film may be permeable to moisture over at least a portion of the transparent film. Optionally, the transparent film may be at least partially or wholly waterproof over at least a portion of the transparent film. Optionally, the transparent film may be impermeable to bacteria over at least a portion of the transparent film.

Optionally, the adhesive may be pressure sensitive. The adhesive may be formed at least in part with an acrylate copolymer adhesive.

Optionally, the aspect ratio of the length to the width is greater than 1.

An embodiment of the disclosure is a method of using the dressing comprising removing the backing from the dressing; holding the dressing by the protective tabs; placing the dressing over a catheter insertion site; applying pressure to the dressing; and removing the stabilizing layer from the dressing.

Optionally, the dressing may be used for catheter stabilization. The dressing may include a stabilizing layer from the catheter stabilization device by lifting a portion of the stabilizing layer at a split.

The dressing may be applied by one of a clinician and a patient.

The dressing may further comprise placing a piece of tape over a hub of a catheter at the catheter insertion site prior to placing the dressing over the catheter insertion site.

The dressing may be removed by lifting the dressing away from the patient at one or both of the protective tabs.

A method of manufacturing the dressing may comprise applying an adhesive to a portion of the transparent film.

A system or kit of the protective dressing may include a safety needle set, an automatic injector, and the dressing together. The safety needle set may comprise a needle assembly that includes a medical needle, a main body, and at least one wing configured to receive the medical needle.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which.

DETAILED DESCRIPTION

Figure 1:
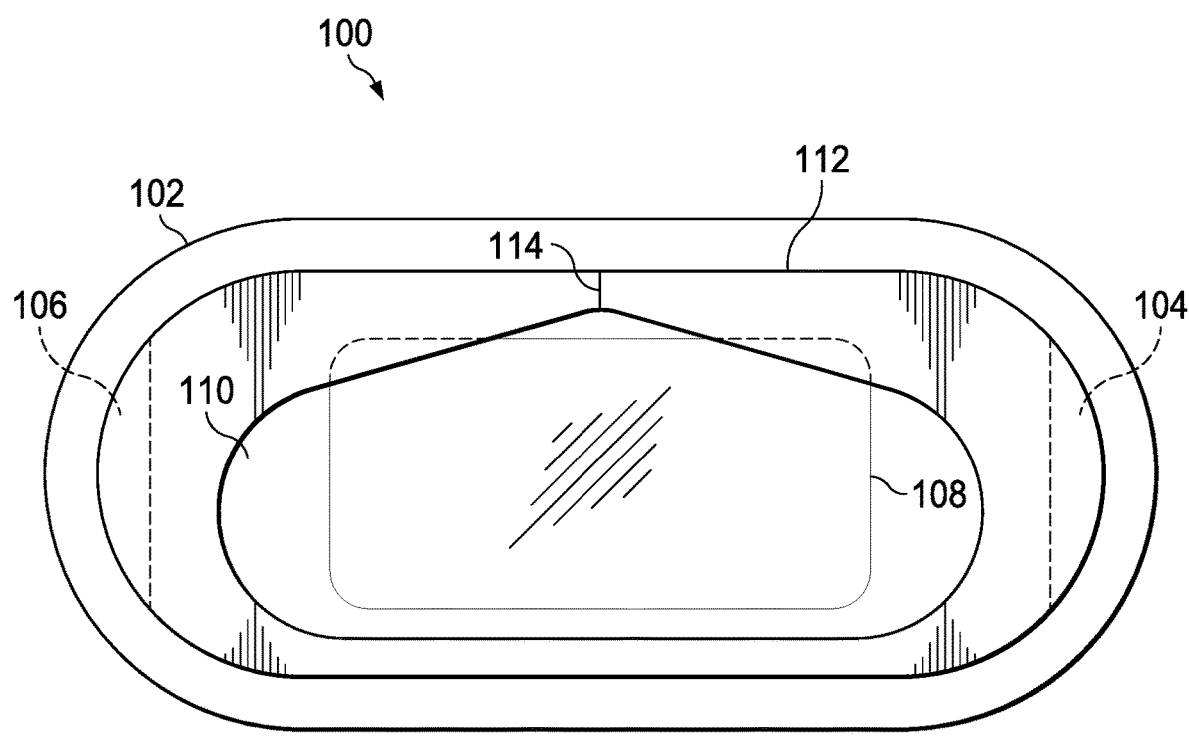
FIG. 1 illustrates an embodiment of the dressing.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary 3rd Edition.

A transparent dressing may be used for securing a catheter at an injection site on a patient. A portion of the transparent dressing does not have adhesive over at least a portion of the dressing to allow placement of the dressing over the catheter without risk of the adhesive affecting the placement of the catheter at the time of removal of the dressing. The transparent dressing may include tabs without adhesive on the outer edges for ease of use by clinicians and patients. The transparent window provides the ability to check the injection site without removing the dressing.

Optionally, the transparent or windowed dressing may be used to secure a medical needle, including a needle set or a needle assembly, at the injection site on a patient. The transparent or windowed dressing may be utilized with a device for protecting a user from a sharp tip of a medical needle and an automatic insertor. Optionally, the transparent or windowed dressing may be used to secure the wings of a device for protecting a user from the sharp point of a medical needle.

A catheter stabilization device may include a dressing. The dressing optionally comprises a backing; a transparent film adjacent to the backing wherein a portion of the transparent film does not have an adhesive coating and a portion of the transparent film does have an adhesive coating; at least one and, in some instances, a plurality (at least two or more) protective tabs may be positioned adjacent to the transparent film. A plurality of protective tabs may be positioned at any point around the transparent dressing, including, but not limited to at opposite ends of the transparent film. The at least one protective tab may not have an adhesive coating; and a stabilizing layer may be adjacent to the transparent film. Optionally the stabilizing layer may extend at least partially around and, in some examples, fully around the upper perimeter of the transparent film. Optionally, the stabilizing layer may be present across only a portion of the upper surface of the transparent film. The stabilizing layer may include an interior border. The interior border may include one side that is dissimilar to the opposite side of the stabilizing layer. The interior border may include one side with at least one split in the stabilizing layer.

A method of using the catheter stabilization device comprises removing a backing from the catheter stabilization device; holding the catheter stabilization device by the protective tabs; placing the catheter stabilization device over the catheter insertion site; applying pressure to the catheter stabilization device; and removing the stabilizing layer from the catheter stabilization device.

A catheter and needle set that includes a transparent dressing may be used to provide infusion therapy. The transparent dressing may be placed over the injection site and at least the medial needle of the needle set.

FIG. 1 illustrates an embodiment of a dressing 100. A backing 102 may be applied or releasably coupled to at least a portion and, in some instances define an outermost perimeter of the dressing 100 while the backing 102 is present. The backing 102 may prevent the transparent film 110 from sticking to an unintended surface. The backing 102 may be slick, i.e., have no adhesive and/or a very low coefficient of friction, on at least one side to allow easy removal of the dressing 100 from the backing 102. The backing 102 optionally may be a coated paper. A portion of the transparent film 110 may be coated with an adhesive, leaving a portion of the transparent film 110 without an adhesive. By transparent it is meant that at least 25% of available light is passable through the transparent film 110 and, more preferably, at least 50% of available light is passable through the transparent film 110, and, in some instances, at least 75% of available light is passable through the transparent film 110, or, alternatively at least 90% of available light is passable through the transparent film 110.

At least one protective tab or, in some instances, a plurality of protective tabs protective tabs 104 and 106 may include at least a portion and, optionally, the entirety of the protective tabs 104 and 106 may not be coated with an adhesive in order to provide a location for a user to touch the dressing 100 without the dressing 100 sticking to a user's hands when applying or removing the dressing from the patient's skin. In an embodiment, that area is not coated with adhesive. In an embodiment, that area was coated with an adhesive, but another material was placed over the adhesive to provide a non-adhesive surface.

The dressing 100 may include at least one window 108. The at least one window 108 may include a section of the transparent film 110 that is not coated with an adhesive. Optionally, the window may include that portion of the transparent film 110 that is not coated with adhesive. Optionally, the window 108 may include a portion of the transparent film 110 that was coated with adhesive and includes another material that may be placed over the adhesive to provide a non-adhesive surface to that portion of the transparent film 110.

A stabilizing layer 112 may be present on a surface of the transparent film 110 opposite from the backing 102. The stabilizing layer 112 may be a heavy paper provided to give structure and ease of handling when applying the dressing to a patient. Optionally, the stabilizing layer 112 may be present over at least of portion of the transparent film 110. The stabilizing layer 112 may be present at at least a portion of the perimeter of the transparent film 110 and, in some instances, substantially (75% or more) all of the perimeter. The stabilizing layer 112 may include an interior border in which one side of the interior border is dissimilar to an opposite side of the interior border. A split or preformed cut or perforation 114 may be present in the stabilizing layer 112. The split 114 may provide a place for a user to begin to separate the stabilizing layer 112 from the transparent film 110.

Figure 2:
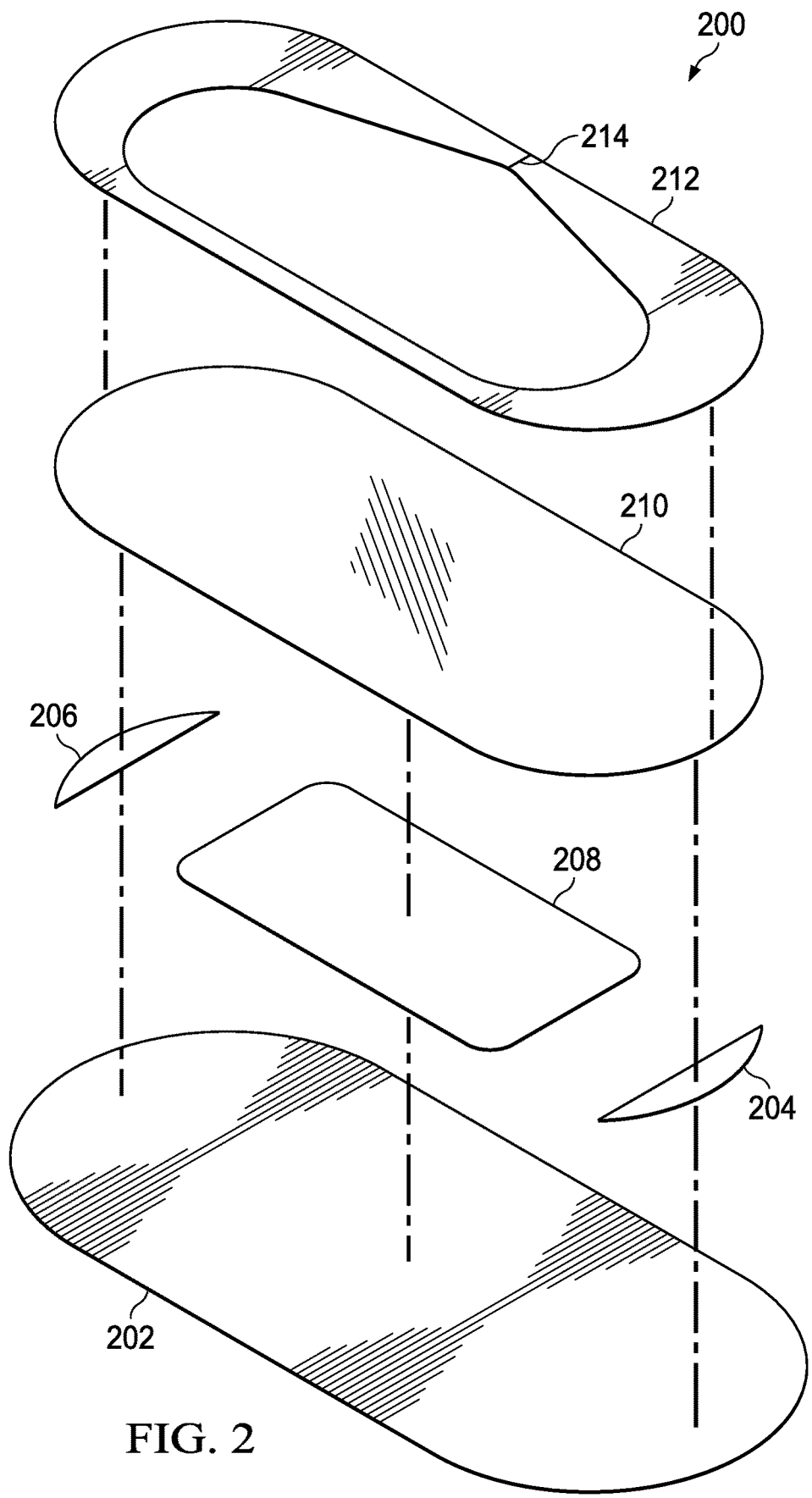
FIG. 2 illustrates an embodiment of different areas of the dressing.

FIG. 2 illustrates an embodiment of different areas of a dressing 200. A backing 202 may be present to prevent a transparent film 210 from sticking to unintended surfaces. The backing 202 may be slick or have a low coefficient of friction on at least one side to allow easy removal of the dressing 200 from the backing 202. Optionally, the backing 202 may be a coated paper. A portion of the transparent film 210 may be coated with an adhesive. The transparent film may include any of the transparencies as defined above. At least one protective tab and, in some instances a plurality of protective tabs 204 and 206 may not be coated with adhesive in order to provide a location for a user to touch the dressing 200 without the dressing sticking to the user's hands. In an embodiment, that area is not coated with adhesive. In an embodiment, that area was coated with an adhesive, but another material was placed over the adhesive to provide a non-adhesive surface.

Optionally, at least one window 208 is a section of the transparent film that is not coated with adhesive. Optionally, the at least one window 208 may include an area that was coated with an adhesive, but another material is placed over the adhesive to block or cover the adhesive so as to provide a non-adhesive surface.

A stabilizing layer 212 may be present on the opposite surface of the transparent film 210 from the backing 202. A stabilizing layer 212 may include a portion that is a heavy paper provided to give structure and ease of handling when applying the dressing to a patient. The stabilizing layer 212 may be present at at least a portion of the perimeter of the transparent film 210 and, in some instances, substantially (75% or more) all of the perimeter. The stabilizing layer 212 may include an interior border in which one side of the interior border is dissimilar to an opposite side of the interior border. A split or preformed cut or perforation 214 may be present in the stabilizing layer 212. The split 214 may provide a place for a user to begin to separate the stabilizing layer 212 from the transparent film 210.

Figure 3:
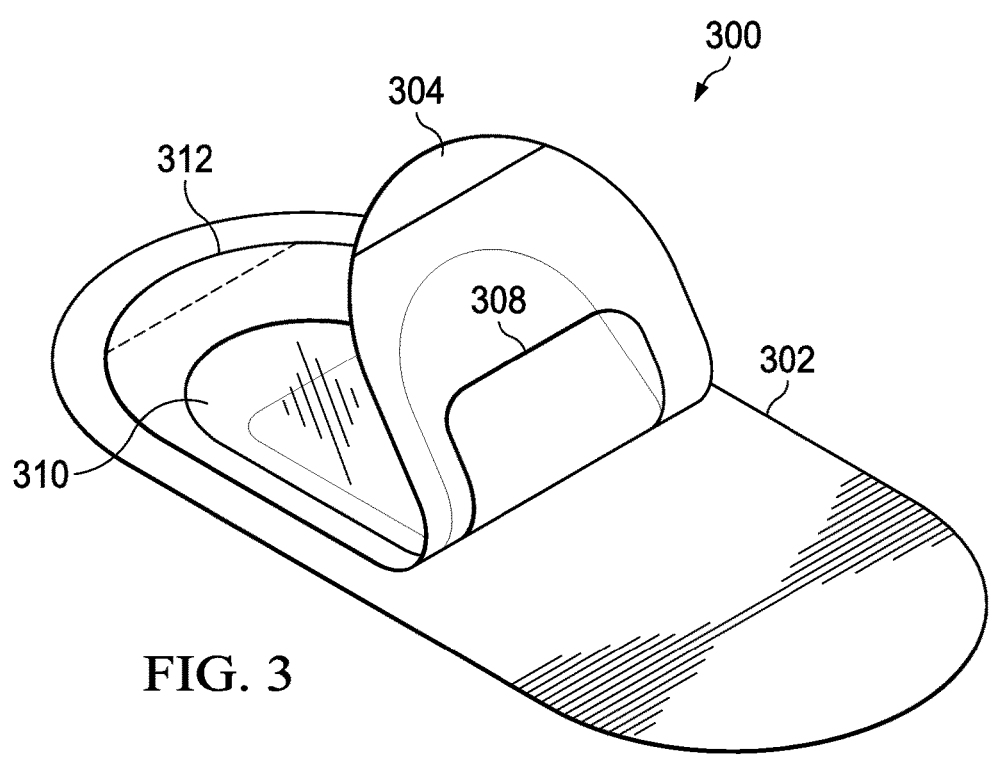
FIG. 3 illustrates an embodiment of the dressing partially removed from the backing.

FIG. 3 illustrates an embodiment of the dressing 300 partially removed from a backing 302. The backing 302 may prevent the transparent film 310 from sticking to unintended surfaces.

The backing 302 may be slick or have a low coefficient of friction on at least one side to allow easy removal of the dressing 300 from the backing 302. Optionally, the backing 302 may be a coated paper. A portion of the transparent film 310 may be coated with an adhesive. The transparent film may include any of the transparencies as defined above. At least one protective tab and, in some instances a plurality of protective tabs 304 may not be coated with adhesive in order to provide a location for a user to touch the dressing 300 without the dressing sticking to the user's hands and skin site of infusion to facilitate lifting and removing the dressing. In an embodiment, that area is not coated with adhesive. In an embodiment, that area was coated with an adhesive, but another material was placed over the adhesive to provide a non-adhesive surface.

Optionally, at least one window 308 is a section of the transparent film that is not coated with adhesive. Optionally, the at least one window 308 may include an area that was coated with an adhesive, but another material is placed over the adhesive to provide a non-adhesive surface.

A stabilizing layer 312 may be present on the opposite surface of the transparent film 310 from the backing 302. A stabilizing layer 312 may include a portion that is a heavy paper provided to give structure and ease of handling when applying the dressing to a patient. The stabilizing layer 312 may be present at at least a portion of the perimeter of the transparent film 310 and, in some instances, substantially (75% or more) all of the perimeter. The stabilizing layer 312 may include an interior border in which one side of the interior border is dissimilar to an opposite side of the interior border. A split or preformed cut or perforation may be present in the stabilizing layer 312. The split may provide a place for a user to begin to separate the stabilizing layer 312 from the transparent film 310.

Optionally, the dressing 100, 200, 300 may be hypoallergenic. The transparent film 110, 210, 310 may be at least one of a polymeric film, a polyester, a polyurethane film, and combinations thereof. The transparent film 110, 210, 310 may be permeable to moisture. The transparent film 110, 210, 310 may be waterproof. The transparent film 110, 210, 310 may be impermeable to bacteria. Optionally, the adhesive applied to the transparent film 110, 210, 310 may be pressure-sensitive. The adhesive may be an acrylate copolymer adhesive. Optionally, the dressing 100, 200, 300 may be sterile.

In an embodiment, the dressing has a window portion without adhesive to prevent the dressing from sticking to the catheter and needle at the insertion site. In an embodiment, the dressing has a window portion without adhesive to prevent the dressing from sticking to the wings of a needle set designed to protect the user from the sharp tip of the needle.

The dressing 100, 200, 300 may be manufactured by applying adhesive only to a portion of the transparent film 110, 210, 310. Optionally, there may be window 108, 208, 308 without adhesive that is present on the transparent film 110, 210, 310. During manufacture, the window 108, 208, 308 may be blocked or covered to prevent adhesive from adhering to the window 108, 208, 308 while adhesive is being applied to the remaining unblocked or uncovered portion of the transparent film 110, 210, 310. The adhesive may be applied in a pre-set shape to the transparent film 110, 210, 310. Optionally, the dressing can be manufactured by any method known in the art.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A protective dressing comprising:
   a backing having a rectangular shape with first and second semicircles on opposing lateral ends;
   a transparent film releasably adjacent to the backing and having a shape complimentary to and smaller than the backing;
   at least one protective tab positioned adjacent to the transparent film; and,
   a stabilizing layer adjacent to the transparent film;
   wherein:
      the stabilizing layer overlays and covers a subset of a rectangular window within the transparent film;
      the stabilizing layer includes an opening extending longitudinally in relation to the transparent film and parallel to a longer side of the rectangular window and having a shape in which opposing circular ends are connected, on a first side, by way of a straight line and connected, on a second side, by way of two lines connected at an obtuse angle;
      the stabilizing layer includes a split extending from a vertex of the obtuse angle on an inner edge to an outer edge of the stabilizing layer, the perforation configured to allow a user to separate the stabilizing layer from the transparent film;
      the window is a portion of the transparent film that is one of a) does not have an adhesive coating and b)

includes an adhesive coating with another layer placed over the adhesive coating to provide a non-adhesive surface; and a portion of the transparent film does have an adhesive coating.

2. The dressing of claim 1, wherein the at least one protective tab includes a plurality of protective tabs.

3. The dressing of claim 2, wherein the plurality of protective tabs are present at opposite ends of the transparent film.

4. The dressing of claim 1, wherein the at least one protective tab does not have an adhesive coating.

5. The dressing of claim 1, wherein the stabilizing layer is not present across an entire upper surface of the transparent film.

6. The dressing of claim 1, wherein the transparent film is at least one of a polymeric film, a polyester film, a polyurethane film, and combinations thereof.

7. The dressing of claim 1, wherein the transparent film is permeable to moisture.

8. The dressing of claim 1, wherein the transparent film is waterproof.

9. The dressing of claim 1, wherein the transparent film is impermeable to bacteria.

10. The dressing of claim 1, wherein the adhesive coating is pressure sensitive.

11. The dressing of claim 1, wherein the adhesive coating is an acrylate copolymer adhesive.

12. A method of manufacturing the dressing of claim 1, comprising applying an adhesive to a portion of the transparent film.

13. The dressing of claim 1, wherein the stabilization layer only covers two of four corners of the rectangular window.

14. A method of using the dressing of claim 1, comprising:
removing the backing from the dressing;
holding the dressing by the at least one protective tab;
placing the dressing over a catheter insertion site on a patient;
applying pressure to the dressing; and
removing the stabilizing layer from the dressing.

15. The method of claim 14, further comprising placing the window over the catheter insertion site.

16. The method of claim 14, wherein removing the stabilizing layer from the dressing is achieved by lifting a portion of the stabilizing layer at the split.

17. The method of claim 14, further comprising placing a piece of tape over the hub of a catheter at the catheter insertion site prior to placing the dressing over the catheter insertion site.

18. The method of claim 14, further comprising removing the dressing away from the site on the patient by the at least one protective tab.

19. The method of claim 14, wherein the at least one protective tab does not adhere to a skin of the patient.

* * * * *